US00PP30390P2

(12) United States Plant Patent
Pieters

(10) Patent No.: US PP30,390 P2
(45) Date of Patent: Apr. 16, 2019

(54) ***CHRYSANTHEMUM* PLANT NAMED 'G19FON06PI'**

(50) Latin Name: ***Chrysanthemum* X *morifolium***
Varietal Denomination: G19FON06PI

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 15/732,911

(22) Filed: Jan. 13, 2018

(51) Int. Cl.
*A01H 5/02* (2018.01)

(52) U.S. Cl.
USPC ..... Plt./287

(58) Field of Classification Search
USPC ..... Plt./287, 291, 292
CPC ..... A01H 5/0255; A01H 5/02; A01H 5/00; A01H 6/1424; A01H 6/14
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'G19FON06PI', characterized by its upright, outwardly spreading and uniformly rounded plant habit; vigorous growth habit; freely branching habit; dense and full plant habit; dark green-colored leaves; uniform and freely flowering habit; long flowering period; and decorative-type inflorescences with greyed purple-colored ray florets.

1 Drawing Sheet

Botanical designation: *Chrysanthemum* X *morifolium*.
Cultivar denomination: 'G19FON06PI'.

BACKGROUND OF THE INVENTION

The present invention relates to a new and distinct cultivar of *Chrysanthemum* plant, botanically known as *Chrysanthemum* X *morifolium* and hereinafter referred to by the name 'G19FON06PI'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in October, 2011 in Oostnieuwkerke, Belgium of a proprietary selection of *Chrysanthemum* X *morifolium* identified as code number GE03, 4640, not patented, as the female, or seed, parent with *Chrysanthemum* X *morifolium* 'Mefisto Purple', disclosed in U.S. Plant Pat. No. 21,896, as the male, or pollen, parent. The new *Chrysanthemum* plant was discovered and selected by the Inventor as a single flowering plant from within the progeny of the stated cross-pollination in a controlled greenhouse environment in Oostnieuwkerke, Belgium in August, 2012.

Asexual reproduction of the new *Chrysanthemum* plant by vegetative terminal cuttings was first conducted in a controlled greenhouse environment in Oostnieuwkerke, Belgium in September, 2014. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'G19FON06PI'. These characteristics in combination distinguish 'G19FON06PI' as a new and distinct *Chrysanthemum* plant:

1. Upright, outwardly spreading and uniformly rounded plant habit; vigorous growth habit.
2. Freely branching habit; dense and full plant habit.
3. Dark green-colored leaves.
4. Uniform and freely flowering habit.
5. Long flowering period.
6. Decorative-type inflorescences with greyed purple-colored ray florets.

Plants of the new *Chrysanthemum* can be compared to plants of the female parent selection. Plants of the new *Chrysanthemum* differ primarily from plants of the female parent selection in the following characteristics:

1. Plants of the new *Chrysanthemum* are more uniform than plants of the female parent selection.
2. Plants of the new *Chrysanthemum* flower earlier than plants of the female parent selection.
3. Ray florets of plants of the new *Chrysanthemum* are darker greyed purple in color than ray florets of plants of the female parent selection.

Plants of the new *Chrysanthemum* can be compared to plants of the male parent, 'Mefisto Purple'. Plants of the new *Chrysanthemum* differ primarily from plants of 'Mefisto Purple' in the following. characteristics:

1. Plants of the new *Chrysanthemum* flower earlier than plants of 'Mefisto Purple'.
2. Ray florets of plants of the new *Chrysanthemum* are flatter than ray florets of plants of 'Mefisto Purple'.
3. Ray florets of plants of the new *Chrysanthemum* are greyed purple in color whereas ray florets of plants of 'Mefisto Purple' are red purple in color.

Plants of the new *Chrysanthemum* can be compared to plants of the *Chrysanthemum* X *morifolium* 'PPP AMIK 09', disclosed in U.S. Plant Pat. No. 21,453. In side-by-side comparisons, plants of the new *Chrysanthemum* differ primarily from plants of 'PPP AMIK 09' in the following characteristics:

1. Plants of the new *Chrysanthemum* are more uniformly rounded than plants of 'PPP AMIK 09'.
2. Plants of the new *Chrysanthemum* flower about two to three weeks earlier than plants of 'PPP AMIK 09'.
3. Ray florets of plants of the new *Chrysanthemum* are greyed purple in color whereas ray florets of plants of 'PPP AMIK 09' are violet in color.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a side perspective view of a typical flowering plant of 'G19FON06PI' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plant, day temperatures ranged from 20° C. to 25° C. and night temperatures ranges from 12° C. to 18° C. Plants were 20 weeks old when the photograph and detailed description were taken. In the following description, color references are made to The Royal Horticultural Society Colour Chart, 2007, Fifth Edition, except where general terms of ordinary dictionary significance are used.

Botanical classification: *Chrysanthemum* X morifolium 'G19FON06PI'.

Parentage:

*Female, or seed, parent.*—Proprietary selection of *Chrysanthemum* X morifolium identified as code number GE03.4640, not patented.

*Male, or pollen, parent.*—*Chrysanthemum* X *morifolium* 'Mefisto Purple', disclosed in U.S. Plant Pat. No. 21,896.

Propagation:

*Type cutting.*—By vegetative tip cuttings.

*Time to initiate roots, summer.*—About two weeks at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants roughly spherical; very freely branching habit, about 20 primary lateral branches develop, each primary lateral branch with multiple secondary branches; pinching enhances lateral branch development; dense and full plant habit; vigorous growth habit; plants flexible, not brittle.

*Plant height.*—About 45 cm.

*Plant width.*—About 60 cm.

*Lateral branches.*—Length: About 30 cm. Diameter: About 2 mm to 3 mm. Internode length: About 3 cm. Strength: Strong, flexible. Texture: Pubescent, fine; longitudinally ridged. Color: Close to 141A.

*Leaves.*—Arrangement: Alternate, simple. Length: About 4.5 cm to 6 cm. Width: About 2.5 cm to 3 cm. Apex: Rounded. Base: Attenuate. Margin: Palmately lobed and serrate, sinuses between lateral lobes divergent to parallel. Texture upper and lower surfaces: Slightly pubescent. Venation: Palmately reticulate. Color: Developing leaves, upper surface: Close to 141A. Developing leaves, lower surface: Close to 139C. Fully expanded leaves, upper surface: Close to 137A; venation, close to 148C. Fully expanded leaves, lower surface: Close to 137C; venation, close to 147B to 147C. Petioles: Length: About 1 cm. Diameter: About 2 mm. Texture, upper and lower surfaces: Slightly pubescent; rough. Color, upper surface: Close to 137A. Color, Tower surface: Close to 137C. Stipules: Length: About 1 cm. Diameter: About 2 mm. Texture, upper and lower surfaces: Slightly pubescent; rough. Color, upper and lower surfaces: Close to 137A.

Inflorescence description:

*Appearance.*—Decorative-type inflorescence form; inflorescences borne on terminals above foliar plane; disc and ray florets arranged acropetally on a capitulum.

*Fragrance.*—Slightly fragrant, pungent.

*Flowering response.*—Under natural season conditions, plants flower in early September in Belgium; flowering response time, about 32 days.

*Postproduction longevity.*—Inflorescences maintain good color and substance for about 38 to 40 days inn outdoor nursery; inflorescences persistent.

*Quantity of inflorescences.*—About 20 to 25 inflorescences develop per lateral branch.

*Inflorescence buds.*—Height: About 6 mm. Diameter: About 8 mm. Shape: Globular. Color: Close to 185D.

*Inflorescence diameter.*—About 6 cm.

*Inflorescence depth (height).*—About 3.5 cm.

*Disc diameter.*—About 7 mm; inconspicuous.

*Receptacle diameter.*—About 3 mm.

*Receptacle height.*—About 2.5 mm to 3 mm.

*Receptacle color.*—Close to 144B.

*Ray florets.*—Length: About 3.5 cm to 5 cm. Width: About 7 mm. Shape: Oval. Apex: Rounded. Base: Attenuate. Margin: Entire. Aspect: Mostly flat. Texture and luster, upper and lower surfaces: Smooth, glabrous; matte. Number of ray florets per inflorescence: About 125 to 150 arranged in about seven whorls. Color: When opening, upper surface: Close to 185D. When opening, lower surface: Close to 51D. Fully opened, upper surface: Close to 185D; distally, close to 56A; color becoming closer to 56A with development. Fully opened, lower surface: Close to 56A; color becoming closer to 56C with development.

*Disc florets*.—Length: About 3 mm. Diameter: About 0.5 mm to 1 mm. Shape: Tubular; apices acute. Number of disc florets per inflorescence: About 60 to 80 massed at the center of the inflorescence. Texture: Smooth, glabrous. Color, immature: Close to 145A. Color, mature: Close to 12A.

*Phyllaries*.—Number of phyllaries per inflorescence: About 25 arranged in two or three whorls. Length: About 4 mm Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 7 cm. Length, seventh peduncle: About 7 cm. Diameter: About 2.5 mm. Angle: About 30° from vertical. Strength: Strong. Texture: Slightly pubescent. Color: Close to 146B.

*Reproductive organs*.—Androecium: Not observed. Gynoecium: Not observed.

*Seeds and fruits*.—To date seed and fruit production have not been observed on plants of the new *Chrysanthemum*.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'G19FON06PI' as illustrated and described.

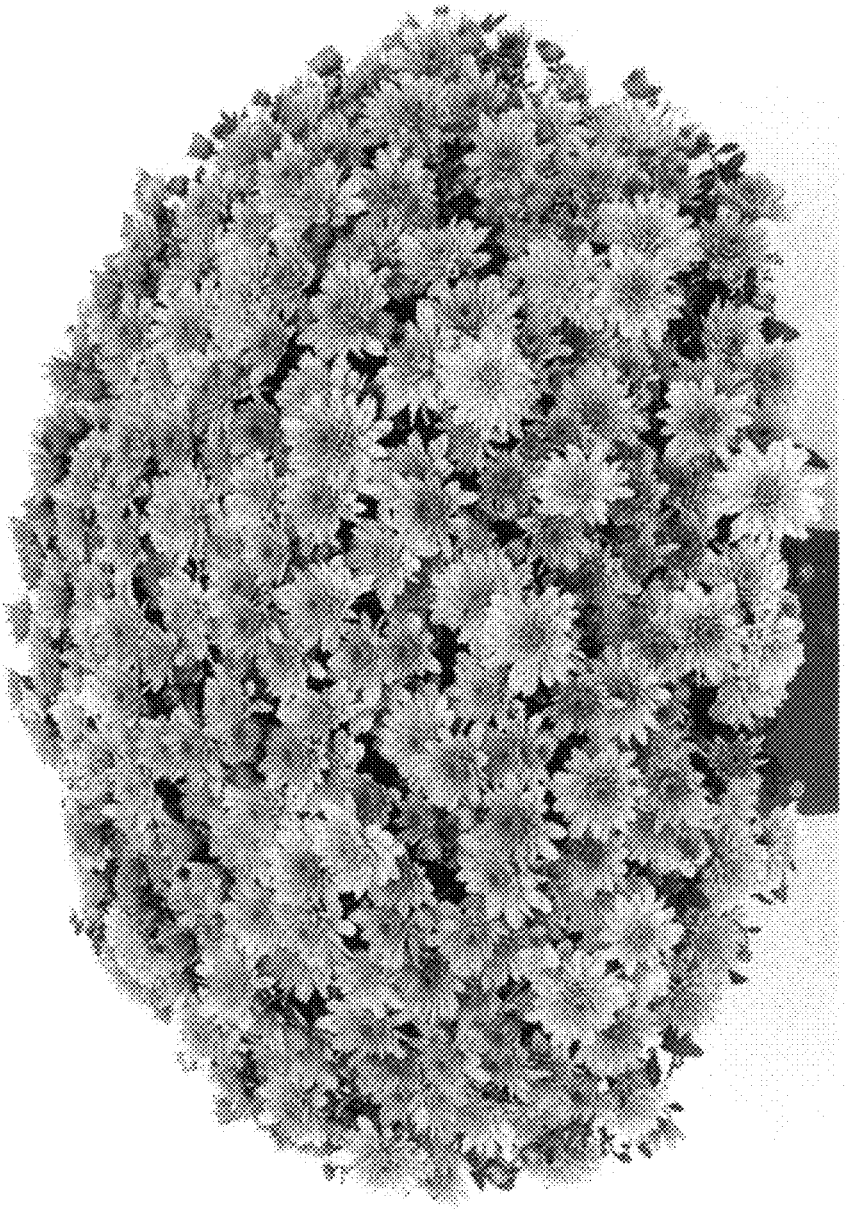

* * * * *